US00PP32898P2

(12) United States Plant Patent
Kobayashi

(10) Patent No.: US PP32,898 P2
(45) Date of Patent: Mar. 16, 2021

(54) **NEW GUINEA *IMPATIENS* PLANT NAMED 'DONGISUSTJAZCO'**

(50) Latin Name: *Impatiens hawkeri*
Varietal Denomination: Dongisustjazco

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/873,885

(22) Filed: Aug. 4, 2020

(51) Int. Cl.
*A01H 5/02* (2018.01)
*A01H 6/16* (2018.01)

(52) U.S. Cl.
USPC ..... Plt./318.7
CPC ..... *A01H 6/165* (2018.05)

(58) Field of Classification Search
USPC ..... Plt./318.7
CPC ..... A01H 6/165
See application file for complete search history.

*Primary Examiner* — Anne Marie Grunberg
(74) *Attorney, Agent, or Firm* — C. Anne Whealy

(57) ABSTRACT

A new and distinct cultivar of *Impatiens* plant named 'Dongisustjazco' characterized by its upright to outwardly spreading and uniformly mounding plant habit; moderately vigorous growth habit; freely branching habit; large variegated leaves with dark green-colored marginal areas surrounding yellow-colored centers; freely flowering habit; large flat flowers that are vivid red in color; and good garden performance.

2 Drawing Sheets

Figure 1:
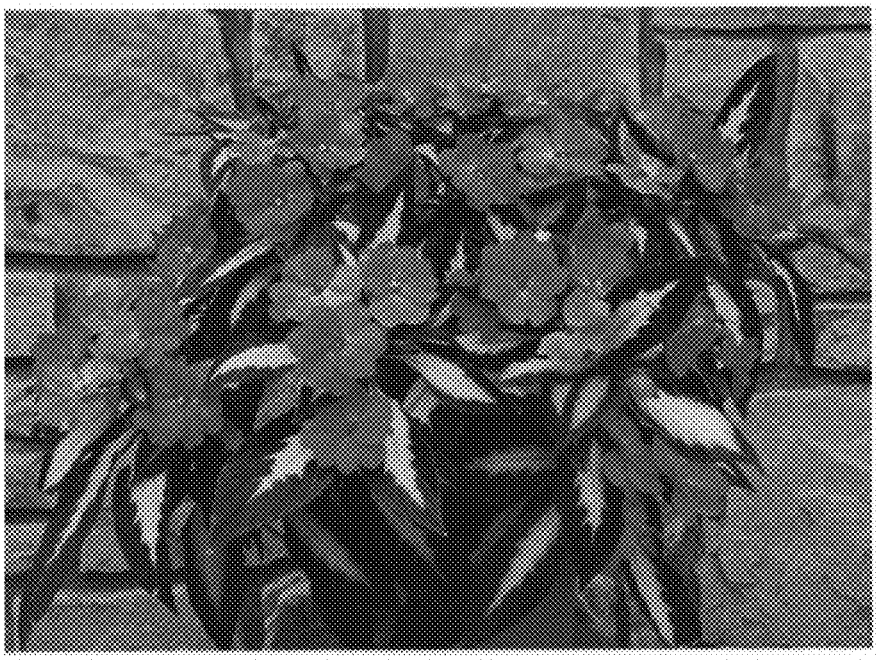

Botanical designation: *Impatiens hawkeri.*
Cultivar denomination: 'DONGISUSTJAZCO'.

CROSS-REFERENCED TO CLOSELY-RELATED APPLICATIONS

Title: New Guinea *Impatiens* Plant Named 'DONGISUSTJAZHOPI'
Applicant: Ruth Kobayashi
Filed: Concurrently with the instant application having application Ser. No. 16/873,884.

STATEMENT REGARDING PRIOR DISCLOSURES BY THE INVENTOR AND APPLICANT

The Inventor and Applicant assert that no sales, publications or advertisements relating to sales, offers for sale or public distribution occurred more than one year prior to the effective filing date of this application. Any information about the claimed plant would have been obtained from a direct or indirect disclosure from the Inventor and/or the Applicant. Inventor and Applicant claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of New Guinea *Impatiens* plant, botanically known as *Impatiens hawkeri* and hereinafter referred to by the name 'Dongisustjazco'.

The new *Impatiens* plant is a product of a planned breeding program conducted by the Inventor in Encinitas, Calif. The objective of the breeding program is to create new early and freely flowering New Guinea *Impatiens* plants with variegated leaves, large attractive flowers and good garden performance.

The new *Impatiens* plant is a naturally-occurring whole plant mutation of a proprietary selection of *Impatiens hawkeri* identified as code number NN-1539, not patented. The new *Impatiens* plant was discovered and selected by the Inventor as a single flowering plant from within a population of plants of the mutation parent selection in a controlled greenhouse environment in Encinitas, Calif. on Dec. 20, 2017.

Asexual reproduction of the new *Impatiens* plant by terminal vegetative cuttings in a controlled greenhouse environment in Encinitas, Calif. since Jul. 20, 2018 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dongisustjazco'. These characteristics in combination distinguish 'Dongisustjazco' as a new and distinct *Impatiens* plant:

1. Upright to outwardly spreading and uniformly mounding plant habit.
2. Moderately vigorous growth habit.
3. Freely branching habit.
4. Large variegated leaves with dark green-colored marginal areas surrounding yellow-colored centers.

5. Freely flowering habit.
6. Large flat flowers that are vivid red in color.
7. Good garden performance.

Plants of the new *Impatiens* can be compared to plants of the mutation parent selection. Plants of the new *Impatiens* differ primarily from plants of the mutation parent selection in flower color as flowers of plants of the new *Impatiens* are vivid red in color whereas flowers of plants of the mutation parent selection purplish pink in color.

Plants of the new *Impatiens* can be compared to plants of *Impatiens hawkeri* 'Dongisustjazhopi', disclosed in a U.S. Plant Patent application filed concurrently having application Ser. No. 16/873,884. Plants of the new *Impatiens* differ primarily from plants of 'Dongisustjazhopi' in flower color as plants of the new *Impatiens* have vivid red-colored flowers whereas plants of 'Dongisustjazhopi' have purplish pink-colored flowers.

Plants of the new *Impatiens* can be compared to plants of *Impatiens hawkeri* 'SAKIMP008', disclosed in U.S. Plant Pat. No. 21,014. In side-by-side comparisons, plants of the new *Impatiens* differ primarily from plants of 'SAKIMP008' in the following characteristics:

1. Plants of the new *Impatiens* are not as vigorous as plants of 'SAKIMP008'.
2. Leaves of plants of the new *Impatiens* are variegated whereas leaves of plants of 'SAKIMP008' are solid green in color.
3. Plants of the new *Impatiens* and 'SAKIMP008' differ in flower color as flowers of plants of the new *Impatiens* are vivid red in color whereas flowers of plants of 'SAKIMP008' are salmon orange in color.

Plants of the new *Impatiens* can also be compared to plants of *Impatiens hawkeri* 'Duemagfi', disclosed in U.S. Plant Pat. No. 23,912. In side-by-side comparisons, plants of the new *Impatiens* differ primarily from plants of 'Duemagfi' in the following characteristics:

1. Leaves of plants of the new *Impatiens* are variegated whereas leaves of plants of 'Duemagfi' are solid green in color.
2. Plants of the new *Impatiens* have smaller flowers than plants of 'Duemagfi'.
3. Plants of the new *Impatiens* and 'Duemagfi' differ in flower color as flowers of plants of the new *Impatiens* are vivid red in color whereas flowers of plants of 'Duemagfi' are light red in color.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet (FIG. 1 of 2) is a side perspective view of a typical flowering plant of 'Dongisustjazco' grown in a container.

Figure 2:
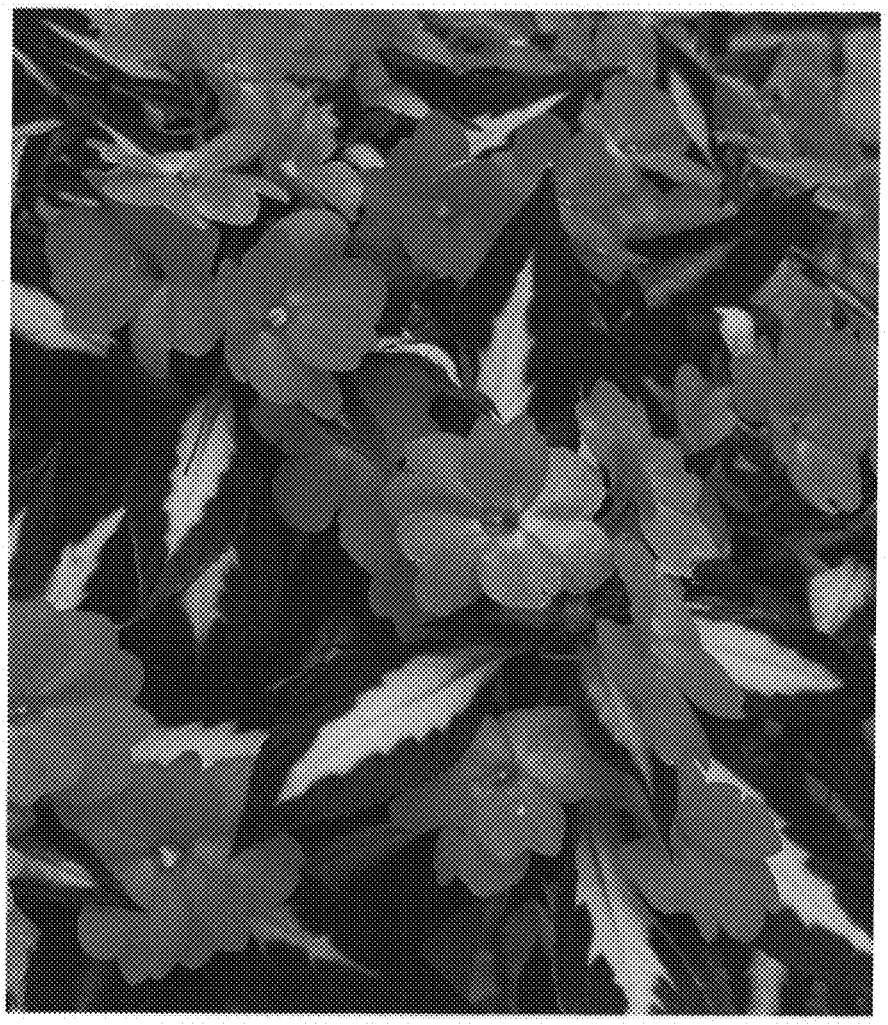

The photograph on the second sheet (FIG. 2 of 2) is a close-up view of a typical flowering plant of 'Dongisustjazco'.

DETAILED BOTANICAL DESCRIPTION

The aforementioned photographs and following observations, measurements and values describe plants grown during the winter and early spring in 19-cm containers in a polyethylene-covered greenhouse in Encinitas, Calif. and under cultural practices typical of commercial New Guinea *Impatiens* production. During the production of the plants, day temperatures averaged 24° C., night temperatures averaged 17° C. and light levels ranged from 3,500 to 4,500 lux. Plants were 18 weeks old when the photographs and description were taken. In the following description, color references are made to The Royal Horticultural Society Colour Chart, 2015 Edition, except where general terms of ordinary dictionary significance are used.

Botanical classification: *Impatiens hawkeri* 'Dongisustjazco'.

Parentage: Naturally-occurring whole plant mutation of a proprietary selection of *Impatiens hawkeri* identified as code number NN-1539, not patented.

Propagation:

*Type*.—By terminal vegetative cuttings.

*Time to initiate roots, summer and winter*.—About five to seven days at day temperatures about 27° C. and night temperatures about 20° C.

*Time to produce a rooted young plant, summer and winter*.—About three weeks at day temperatures about 27° C. and night temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Upright to outwardly spreading and uniformly mounding plant habit; broad inverted triangle in overall shape; freely branching habit; bushy and dense appearance; moderately vigorous growth habit and moderate to rapid growth rate.

*Plant height*.—About 41 cm.

*Plant diameter*.—About 64 cm.

Lateral branch description:

*Branching habit*.—Freely branching with potentially two to three lateral branches developing at every node.

*Length*.—About 33 cm.

*Diameter*.—Thick, about 1.7 cm.

*Internode length*.—About 5 cm to 9 cm.

*Strength*.—Strong, flexible.

*Aspect*.—Initially upright to outwardly spreading, about 45° to 50° from stem axis.

*Texture and luster*.—Smooth, glabrous; semi-glossy.

*Color, developing*.—Close to 146A heavily overlain with close to 59A to 59B.

*Color, fully developed*.—Close to 146A variably overlain with close to 59A to 59B.

Leaf description:

*Arrangement*.—Typically in whorls or opposite; simple.

*Length, largest leaves*.—About 14.25 cm.

*Width, largest leaves*.—About 5.25 cm.

*Shape*.—Obovate.

*Apex*.—Acuminate.

*Base*.—Cuneate.

*Margin*.—Serrate with ciliation.

*Texture and luster, upper surface*.—Smooth, glabrous; slightly glossy.

*Texture and luster, lower surface.*—Smooth, glabrous; semi-glossy.

*Venation pattern.*—Pinnate; arcuate.

*Color.*—Developing leaves, upper surface: Centers, close to 10A to 10B surrounded by close to between 139A and 147A. Developing leaves, lower surface: Centers, close to 9D surrounded by close 147B. Fully expanded leaves, upper surface: Centers, close to 8D surrounded with a narrow area of close to 144A and towards the margins, close to N189A; midvein, proximally, close to 58A to 58B and distally, close to 154D; lateral venation, similar to lamina colors. Fully expanded leaves, lower surface: Centers, close to 11D surrounded with a narrow area of close to 144A and towards the margins, close to 147A; midvein, close to 58A to 58B; lateral venation, similar to lamina colors.

*Petioles.*—Length: About 3.1 cm to 3.3 cm. Diameter: About 4 mm to 5 mm. Texture and luster, upper and lower surfaces: Smooth, glabrous; semi-glossy. Color, upper and lower surfaces: Close to 58A to 58B.

Flower description:

*Flower type and flowering habit.*—Large single axillary flowers that are rounded rectangular in shape; freely flowering habit, typically about three to five fully opened flowers and about two to three flower buds per lateral branch; flowers are flat and positioned above and beyond the foliar plane, flowers typically face mostly upright.

*Flower longevity.*—Flowers typically last about four to seven days on the plant under greenhouse conditions; petals self-cleaning, gynoecium persistent.

*Fragrance.*—None detected.

*Natural flowering season.*—Year-round under greenhouse conditions; in the garden, flowering from spring until fall in California; early flowering habit, plants typically begin flowering about 14 weeks from unrooted cuttings.

*Flower buds.*—Length: About 1.25 cm. Diameter: About 7.25 mm. Shape: Ovoid. Texture and luster: Smooth, glabrous; glossy. Color: Close to 146C to 146D variably overlain with close to 59A to 59B.

*Flower diameter.*—Large, about 4.5 cm by 6 cm.

*Flower depth.*—About 1.75 cm.

*Petals.*—Quantity and arrangement: Five per flower in a single whorl with one banner petal, two lateral petals and two lower petals. Length, banner petal: About 3 cm. Length, lateral petals: About 2.4 cm. Length, lower petals: About 3 cm. Width, banner petal: About 3.5 cm. Width, lateral petals: About 2.1 cm. Width, lower petals: About 3 cm. Shape, all petals: Cordate. Apex, all petals: Emarginate, cordate. Base, all petals: Cuneate. Margin, all petals: Entire, not undulate. Texture and luster, all petals, upper surface: Smooth, glabrous; velvety; slightly glossy; iridescent. Texture and luster, all petals, lower surface: Smooth, glabrous; slightly glossy. Color, all petals: When opening, upper surface: Close to 52A. When opening, lower surface: Close to 52A to 52B. Fully opened, upper surface: Close to 52A; color does not change with development. Fully opened, lower surface: Close to 52B; color does not change with development.

*Sepals.*—Quantity and arrangement: Three in a single whorl; two laterals are opposite and the third modified into an elongated spur. Lateral sepal length: About 1.2 cm. Lateral sepal width: About 7 mm. Lateral sepal shape: Ovate. Lateral sepal apex: Aristate. Lateral sepal base: Obtuse. Lateral sepal margin: Entire, not undulate. Lateral sepal texture and luster, upper and lower surfaces: Smooth, glabrous; moderately glossy. Lateral sepal color, upper surface: Close to 146A. Lateral sepal color, lower surface: Close to 146A variably overlain with close to 58A Spur length: About 4.75 cm. Spur diameter: At flower, about 2 mm; at apex, less than 1 mm. Spur shape: Acicular, curved. Spur texture and luster: Smooth, glabrous; moderately glossy. Spur color: Close to 59A.

*Peduncles.*—Length: About 3.5 cm to 3.7 cm. Diameter: About 2 mm. Angle: About 30° to 45° from stem axis. Strength: Strong; flexible. Texture and luster: Smooth, glabrous; semi-glossy. Color: Close to 58A to 58B.

*Reproductive organs.*—Stamens: Quantity: Five fused at anthers; filaments free. Filament length: About 4.5 mm. Filament color: Close to 158A. Anther length: About 2.75 mm. Anther shape: Oblong. Anther color: Close to N155B. Pollen amount: Moderate. Pollen color: Close to 158A. Pistils: Quantity per flower: One. Pistil length: About 4.75 mm. Stigma shape: Crested. Stigma color: Close to 144A. Style length: About 3.75 mm. Style color: Close to 144A. Ovary color: Close to 144A.

*Seeds and fruits.*—To date, seed and fruit production has not been observed on plants of the new *Impatiens.*

Pathogen & pest resistance: To date, plants of the new *Impatiens* have not been observed to be resistant to pathogens and pests common to *Impatiens* plants.

Garden performance: Plants of the new *Impatiens* have been observed to have good garden performance, to perform well in shade and sun exposures and to tolerate temperatures ranging from about 5° C. to about 40° C.

It is claimed:

1. A new and distinct *Impatiens* plant named 'Dongisustjazco' as illustrated and described.

* * * * *